United States Patent [19]

Inui et al.

[11] Patent Number: 5,700,754
[45] Date of Patent: Dec. 23, 1997

[54] BARIUM/CALCIUM CATALYST AND A PROCESS FOR PRODUCING THE SAME

[75] Inventors: Kanichiro Inui; Shunji Oshima, both of Ichihara, Japan

[73] Assignee: Chisso Corporation, Osaka, Japan

[21] Appl. No.: 543,999

[22] Filed: Oct. 17, 1995

[30] Foreign Application Priority Data

Oct. 18, 1994 [JP] Japan .............................. HEI6-278366
Mar. 9, 1995 [JP] Japan .............................. HEI7-078307

[51] Int. Cl.$^6$ ............................................. B01J 23/02
[52] U.S. Cl. ............................................. 502/340
[58] Field of Search .................................. 502/340

[56] References Cited

U.S. PATENT DOCUMENTS

| | | | |
|---|---|---|---|
| 1,914,558 | 6/1933 | Craver | 502/340 |
| 3,763,162 | 10/1973 | Kasibick | 502/340 |

FOREIGN PATENT DOCUMENTS

| | | | |
|---|---|---|---|
| 62-267243 A | 11/1987 | Japan | 502/340 |
| 404018042 | 1/1992 | Japan | 502/340 |

*Primary Examiner*—Glenn Caldarola
*Assistant Examiner*—Naoline Preisch
*Attorney, Agent, or Firm*—Fay, Sharpe, Beall, Fagan, Minnich & McKee

[57] ABSTRACT

A catalyst which causes no occurrence of waste water due to neutralization, water-washing, etc. and can yield the objective product with a high activity and a superior selectivity is provided, and when a specified barium-supporting calcium oxide or a composite oxide of barium oxide with calcium oxide is used as catalyst, such a catalyst is applicable, for example, to a production of a carbonyl compound derivative from a carbonyl compound.

11 Claims, No Drawings

BARIUM/CALCIUM CATALYST AND A PROCESS FOR PRODUCING THE SAME

BACKGROUND OF THE INVENTION

1. Field of the Invention

This invention relates to a solid basic catalyst, a process for producing the same and a process for producing a carbonyl compound derivative using the same. More particularly, it relates to a catalyst composed of solids containing barium and calcium as constituent elements thereof.

2. Description of the Related Prior Art

When a reaction is carried out using a base as a catalyst, alkali metal hydroxides represented by sodium hydroxide has been broadly used. However, the reaction using the alkali metal hydroxides is a homogeneous reaction, and a large quantity of waste water occurs due to neutralization, water-washing, etc. carried out after the reaction. In a case of a process for producing a glycol monoester from an aldehyde, as one of reaction using a base catalyst, Japanese patent publication No. Sho 58-65245 wherein an alkaline earth metal oxide is used, discloses only barium oxide or magnesium oxide in its Examples, and the reaction using barium oxide exhibits a high catalytic activity, but the selectivity of glycol monoester as product is low. On the other hand, in the reaction using magnesium oxide, the activity of the catalyst is low. In the case of a reaction using a carboxylic acid salt as catalyst, since an organic compound other than the reaction compounds is used, there is a possibility that the compound mixes in a product. Further, in the cases of producing diacetone alcohol from acetone or producing a dimer aldehyde from an aldehyde, too, when a reaction is carried out using a catalyst disclosed in Applied Catalysis, 59 (1990), 291–309, which is a known compound, it has been impossible to obtain a sufficient catalytic activity. As described above, according to conventional catalysts, a large quantity of waste water occurred, or it has been difficult to obtain a sufficient catalytic activity or a sufficient selectivity of product.

Further, in general, when a reaction is carried out using a heterogeneous solid catalyst system, the reaction is superior to a reaction using a homogeneous catalyst system, in that (1) operations of neutralization of catalyst, water washing, etc. are unnecessary, and waste water is absent or its quantity is very small;
(2) it is possible to reuse the catalyst; and
(3) a high selectivity is rather easily obtained.

Thus, when a heterogeneous solid catalyst system is used to obtain the objective product as compared with a homogeneous system catalyst, it is expected that the process is more simple; the cost of a plant therefor is cheaper; and a higher yield is obtained. However, it is the present status that a solid catalyst having a high activity and a high selectivity has not yet been found.

The object of the present invention is to provide an efficient solid catalyst capable of obtaining the objective product with a high selectivity.

SUMMARY OF THE INVENTION

The present inventors have found that when a specified solid substance containing barium and calcium as constituent elements in a specified proportion is used as catalyst, it is possible to produce the objective product with a high activity and a high selectivity.

The present invention has the following aspects (1) to (16):

(1) A solid basic catalyst comprising barium and calcium as constituent elements thereof, the barium content thereof being 0.09 to 10% by weight, and the ratio of the calcium content to the barium content being in the range of 6.4 to 793.

(2) A solid basic catalyst according to item (1), wherein the solid basic catalyst is barium-supporting calcium oxide.

(3) A solid basic catalyst according to item (1), wherein said solid basic catalyst is a composite oxide of barium oxide and calcium oxide.

(4) A solid basic catalyst composed of barium-supporting calcium oxide, obtained by adding at least one kind of nitrate, hydroxide or an organic acid salt of barium or an aqueous solution of the foregoing, to a suspension obtained by dispersing calcium hydroxide or calcium oxide or these compounds in water, followed by drying the resulting mixture and subjecting the dried material to thermal decomposition at 500° to 1200° C. in vacuum, an inert gas or air, barium being contained in a range of 0.1 to 10% by weight, and the ratio of the calcium content to the barium content being in the range of 6.4 to 713.

(5) A solid basic catalyst composed of a composite oxide of barium oxide and calcium oxide, obtained by adding a compound containing carbonate ion, to an aqueous solution containing at least one kind of nitrate, hydroxide or an organic salt of barium and at least one kind of nitrate or an organic acid salt of calcium, followed by drying the resulting precipitate, and subjecting the dried material to thermal decomposition at 600° to 1200° C. in vacuum, an inert gas or air, barium being contained in a range of 0.09 to 9% by weight and calcium being contained in a ratio of the calcium content to the barium content of 7.2 to 793.

(6) A solid basic catalyst composed of a composite oxide of barium oxide and calcium oxide, obtained by adding a compound containing carbonate ion, to a an aqueous solution containing at least one kind of nitrate, hydroxide or an organic acid salt of barium and at least one kind of nitrate or an organic acid salt of calcium, followed by drying the resulting precipitate, and subjecting the resulting precursor containing a calcium carbonate of vaterite structure, to thermal decomposition at 600° to 1200° C. in vacuum, an inert gas or air, barium being contained in a range of 0.09 to 9% by weight and calcium being contained in a ratio of the calcium content to the barium content of 7.2 to 793.

(7) A solid basic catalyst composed of a composite oxide of barium oxide and calcium oxide, obtained by impregnating calcium carbonate with a an aqueous solution of at least one kind of nitrate, hydroxide or an organic acid salt of barium, followed by drying the resulting material, and subjecting the dried material to thermal decomposition at a temperature of 600° to 1200° C. in vacuum, an inert gas or air, barium being contained in 0.09 to 9% by weight and calcium being contained in a ratio of calcium content to barium content within a range of 7.2 to 793.

(8) A process for producing a solid basic catalyst composed of barium-supporting calcium oxide, which process comprises adding an aqueous solution of at least one kind of nitrate, hydroxide or an organic acid salt of barium, to a suspension having calcium hydroxide or calcium oxide or these compounds dispersed in water, followed by drying the mixture and subjecting the dried material to thermal decomposition at 500° to 1200° C. in vacuum, an inert gas or air, barium being contained in a quantity of 0.09 to 9% by weight and the ratio of the calcium content to the barium content being in a range of 6.4 to 713.

(9) A process for producing a solid basic catalyst composed of a composite oxide of barium oxide and calcium oxide, which process comprises adding a carbonate ion-containing compound to an aqueous solution composed of at least one kind of nitrate hydroxide or an organic acid salt of barium and nitrate, or an organic acid salt of calcium, followed by drying the resulting precipitate and subjecting the dried material to thermal decomposition at 600° to 1200° C. in vacuum, an inert gas or air, the barium content being. 0.09 to 9% by weight and the ratio of the calcium content to the barium content being in the range of 7.2 to 793.

(10) A process for producing a solid basic catalyst composed of a composite oxide of barium oxide and calcium oxide, which process comprises adding a carbonate ion-containing compound to a solution composed of at least one kind of nitrate, hydroxide or an organic acid salt of barium and at least one kind of nitrate or an organic acid salt of calcium, followed by drying the resulting precipitate and subjecting the resulting precursor containing calcium carbonate of vaterite structure to thermal decomposition at 600° to 1200° C. in vacuum, an inert gas or air, the barium content being 0.09 to 9% by weight and the ratio of the calcium content to the barium content being in the range of 7.2 to 793.

(11) A process for producing a solid basic catalyst composed of a composite oxide of barium oxide and calcium oxide, which process comprises impregnating calcium carbonate with an aqueous solution composed of at least one kind of nitrate, hydroxide or an organic acid salt of barium, followed by drying the resulting material, and subjecting the resulting dried material to thermal decomposition at 600° to 1200° C. in vacuum, an inert gas or air, the barium content being 0.09 to 9% by weight, and the ratio of the calcium content to the barium content being in a range of 7.2 to 793.

(12) A process for producing a carbonyl compound derivative from a carbonyl compound, which process uses a solid basic catalyst according to either one of items (1) to (7).

(13) A process according to item (12), wherein said carbonyl compound is an aldehyde of 4 to 8 carbon atoms.

(14) A process according to item (12), wherein said carbonyl compound is isobutylaldehyde and said carbonyl compound derivative is 2,2,4-trimethyl-1,3-pentanediol mono-isobutylate.

(15) A process according to item (12), wherein said carbonyl compound is normal butylaldehyde and said carbonyl compound derivative is 2-ethylhexenal.

(16) A process according to item (12), wherein said carbonyl compound is acetone and said carbonyl compound derivative is diacetone alcohol.

DETAILED DESCRIPTION OF THE INVENTION

The solid basic catalyst used in the present invention may be in any solid form such as powdery form, granular form or bulky form, but its size is preferably that of 30 to 450 μ. As to the production of the catalyst of the present invention, the barium-supporting calcium oxide may be obtained by adding at least one kind of nitrate, hydroxide or an organic acid salt of barium or an aqueous solution of the foregoing, preferably an aqueous solution of barium nitrate or barium hydroxide, to a suspension obtained by dispersing calcium hydroxide, calcium oxide or these in water, preferably to a calcium hydroxide-water suspension, followed by drying the resulting mixture and further subjecting the dried material to thermal decomposition at 500° to 1200° C., preferably 600° to 1000° C., the weight of barium in the solid catalyst being preferably 0.1 to 10% by weight and the ratio of the calcium content to the barium content being preferably 6.4 to 713. If the temperature of the thermal decomposition is lower than 500° C., hydroxide or nitrate is not completely decomposed, while if the temperature exceeds 1200° C., the activity of the catalyst lowers notably due to its sintering.

In the present invention, the composite oxide of barium oxide and calcium oxide may be a precursor formed as a precipitate when a carbonate ion-containing compound is added to a solution of at least one kind of nitrate, hydroxide or an organic acid salt such as acetic acid salt of barium and at least one kind of nitrate or an organic acid salt such as acetic acid salt of calcium, preferably a precursor containing calcium carbonate of vaterite structure. Such a precursor or solids obtained by impregnating calcium carbonate with a solution of at least one kind of nitrate, hydroxide or an organic acid salt of barium such as acetic acid salt, are dried, followed by subjecting the dried material to thermal decomposition at 600° to 1200° C., preferably 800° to 1000° C., the weight of barium in the solid catalyst being preferably 0.09 to 9% by weight and the ratio of calcium content to barium content being preferably 7.2 to 793. If the temperature of the thermal decomposition is lower than 600° C., a sufficient activity cannot be obtained since the carbonate is not completely decomposed, while if the temperature exceeds 1200° C., the catalyst activity lowers notably due to the sintering of the catalyst.

When the barium content is lower than 0.09%, the selectivity of the objective product is low, while when it exceeds 10% by weight, the catalytic activity lowers.

As to the ratio of calcium content to barium content, for example, if the barium content is specified in the barium-supporting calcium oxide compound or the composite compound of barium oxide-calcium oxide, it is also possble to easily calculate the ratio from the above value. If the ratio of the calcium content to the barium content is outside the range of 6.4 to 793, the resulting properties are inferior to the superior properties well-balanced between the high activity and high selectivity, as exhibited in the present invention.

The atmosphere at the time of the thermal decomposition is not particularly limited. Namely, it is possible to carry out the decomposition under reduced pressure, in an inert gas or in air. Preferably, it is carried out under reduced pressure.

When the objective compound is produced using the solid catalyst of the present invention, the quanties of acid and water contained as impurities, in the carbonyl compound as a raw material, are preferred to be small, but when the acid content is 1% by weight or less and the water content is 5% by weight or less, it is possible to sufficiently use the compound in the present invention.

As the carbonyl compound used in the present invention, aldehydes, preferably aldehydes of 4 to 8 carbon atoms, such as isobutylaldehyde, normal butylaldehyde, 2-ethylbutylaldehyde, 2-ethylhexylaldehyde, etc. can be exemplified, and acetone, too, can be preferably used, but the present invention is not limited to these compounds.

The catalyst of the present invention can be preferably used for producing carbonyl compound derivatives, and particularly when 2,2,4-trimethyl-1,3-pentanediol monoisobutyrate is produced from isobutylaldehyde, when 2-ethylhexanal is produced from normal-butylaldehyde or when diacetone alcohol is produced from acetone, the catalyst is preferable to be used. Among these, when 2,2,4-trimethyl-1,3-pentanediol monoisobutyrate is produced from isobutylaldehyde, the effectiveness of the catalyst is large, but the present invention is not limited to these.

The catalyst of the present invention is utilizable to either of a continuous system by way of fixed bed or a batch system.

The quantity of the catalyst of the present invention used is in the range of 0.01 to 100% by weight based upon the weight of the reaction solution, but it is not limited to the above. As the barium-supporting calcium oxide, it is preferable to use it in a range of 0.01 to 20% by weight, more preferably 0.05 to 10% by weight, based upon the weight of the reaction solution, in the batch system, for example. As the composite oxide of barium oxide-calcium oxide, it is preferable to use it in a range of 0.01 to 20% by weight, more preferably 0.05 to 10% by weight based upon the weight of the reaction solution, in the batch system, for example.

The reaction temperature at the time of using the catalyst of the present invention can be chosen in a range of 10° to 130° C. When the barium-supporting calcium oxide is used as catalyst, in the case of batch system reaction, it is preferred to react a mixture of the catalyst with the reaction solution at a temperature of 10° to 130° C. for 0.5 to 8 hours. If the temperature is lower than 10° C., the reaction rate is insufficient, while if the temperature exceeds 130° C., the selectivity of the product becomes inferior. When the composite oxide of barium oxide-calcium oxide is used as catalyst, in a batch system reaction, for example, it is preferred to react a mixture of the catalyst with the reaction solution at a temperature of 10° to 130° C. for 0.2 to 3 hours. If the temperature is lower than 10° C., the reaction rate is insufficient, while if it exceeds 130° C., the selectivity of the product becomes inferior.

After the reaction, in order to obtain the objective product from the reaction solution, the catalyst is filtered off from the reaction solution, and then the filtrate is distilled according to a known method.

EXAMPLE

The present invention will be concretely explained by way of Examples and Comparative examples, but the present invention should not be construed to be restricted thereto.

Example 1

Calcium hydroxide ($Ca(OH)_2$, made by Kanto Kagaku) (38.5 g) was suspended in purified water (100 ml), followed by dissolving barium nitrate ($Ba(NO_3)_2$, made by Wako Junyaku) (1.5 g) in purified water (200 ml), adding the resulting solution to the above suspension of calcium hydroxide, mixing them and drying. The resulting white solids (4.0 g) were calcined at 900° C. for one hour in vacuum, followed by cooling the resulting material down to room temperature, to obtain a catalyst containing 3% by weight of barium (3.7 g). The total quantity of the catalyst was transferred into a reactor, followed by adding isobutyraldehyde (200.0 g), stirring the mixture, reacting it at 110° C. for one hour, filtering off the reaction solution and analyzing the filtrate according to gas chromatography. The results are as follows:
Conversion of isobutyraldehyde: 90.7%
Selectivity of 2,2,4-trimethyl-1,3-pentanediol monoisobutyrate (hereinafter abbreviated to CS-12): 89.8%
Yield of CS-12: 81.4%

Example 2

Calcium hydroxide ($Ca(OH)_2$, made by Kanto Kagaku) (37.7 g) was suspended in purified water (100 ml), followed by dissolving barium nitrate ($Ba(NO_3)_2$, made by Wako Junyaku) (2.5 g) in purified water (200 ml), adding the resulting solution to the above suspension of calcium hydroxide, mixing them and drying. The resulting white solids (4.0 g) were calcined at 900° C. for one hour in vacuum, followed by cooling the resulting material down to room temperature, to obtain a catalyst containing 5% by weight of barium (3.9 g). The total quantity of the catalyst was transferred into a reactor, followed by adding isobutyraldehyde (200.0 g), stirring the mixture, reacting it at 110° C. for one hour, filtering off the reaction solution and analyzing the filtrate according to gas chromatography. The results are as follows:
Conversion of isobutyraldehyde: 91.4%
Selectivity of CS-12): 89.1%
Yield of CS-12: 81.4%

Example 3

Calcium hydroxide ($Ca(OH)_2$, made by Kanto Kagaku) (38.9 g) was suspended in purified water (100 ml), followed by dissolving barium nitrate ($Ba(NO_3)_2$, made by Wako Junyaku) (1.1 g) in purified water (200 ml), adding the resulting solution to the above suspension of calcium hydroxide, mixing them and drying. The resulting white solids (4.0 g) were calcined at 700° C. for one hour in vacuum, followed by cooling the resulting material down to room temperature, to obtain a catalyst containing 2% by weight of barium (3.7 g). The total quantity of the catalyst was transferred into a reactor, followed by adding isobutyraldehyde (200.0 g), reacting the mixture with stirring at 110° C. for one hour, filtering off the reaction solution and analyzing the filtrate according to gas chromatography. The results are as follows:
Conversion of isobutyraldehyde: 92.4%
Selectivity of CS-12: 84.0%
Yield of CS-12: 77.4%

Example 4

Calcium hydroxide ($Ca(OH)_2$, made by Kanto Kagaku) (39.2 g) was suspended in purified water (100 ml), followed by dissolving barium nitrate ($Ba(NO_3)_2$, made by Wako Junyaku) (0.5 g) in purified water (200 ml), adding the resulting solution to the above suspension of calcium hydroxide, mixing them and drying. The resulting white solids (4.0 g) were calcined at 700° C. for one hour in vacuum, followed by cooling the resulting material down to room temperature, to obtain a catalyst containing 1% by weight of barium (3.9 g). The total quantity of the catalyst was transferred into a reactor, followed by adding isobutyraldehyde (200.0 g), mixing them and reacting the mixture with stirring at 110° C. for one hour. The reaction solution was filtered off, followed by analyzing the filtrate according to gas chromatography. The results are as follows:
Conversion of isobutyraldehyde: 90.9%
Selectivity of CS-12: 83.8%
Yield of CS-12: 76.2%

Example 5

Calcium nitrate tetrahydrate salt ($Ca(NO_3)_2 \cdot 4H_2O$, made by Wako Junyaku) (122.6 g) and barium nitrate ($Ba(NO_3)_2$, made by Wako Junyaku) (1.7 g) were dissolved in purified water (500 ml), followed by adding a solution obtained by dissolving ammonium carbonate ($(NH_4)_2CO_3$, made by Wako Junyaku) (60.6 g) in purified water (300 ml) to the above solution, filtering off the resulting precipitate, water-washing and drying, to obtain a precursor of vaterite structure which was white solids. The white solids (7.3 g) were calcined at 900° C. for one hour in vacuum, followed by transferring the calcined material into a reactor, adding isobutyraldehyde (200.0 g), stirring the mixture, reacting it at 60° C. for 0.5 hour, filtering off the reaction solution and analyzing the filtrate according to gas chromatography. The results are as follows:
Conversion of isobutyraldehyde: 98.8%
Selectivity of CS-12: 93.8%
Yield of CS-12: 92.7%

Example 6

Calcium carbonate ($CaCO_3$, made by Wako Junyaku) (84.8 g) was suspended in purified water (200 ml), followed by dissolving barium nitrate ($Ba(NO_3)_2$, made by Wako Junyaku) (4.8 g) in purified water (150 ml), adding this solution to the above suspension of calcium carbonate, mixing them and drying. The resulting white solids (7.3 g) were calcined at 900° C., for one hour in vacuum, followed by transferring the resulting material into a reactor, adding isobutyraldehyde (200.0 g), mixing them, reacting at 60° C. for 0.5 hour, filtering off the reaction solution and analyzing the filtrate according to gas chromatography. The results are as follows:
Conversion of isobutyraldehyde: 95.4%
Selectivity of CS-12: 89.7%
Yield of CS-12: 85.6%

Example 7

Calcium carbonate ($CaCO_3$, made by Wako Junyaku) (52.0 g) was suspended in purified water (200 ml), followed by dissolving barium nitrate ($Ba(NO_3)_2$, made by Wako Junyaku) (1.7 g) in purified water (100 ml), adding the resulting solution to the above suspension of calcium carbonate, mixing them and drying. The resulting white solids (7.3 g) were calcined at 900° C., for one hour in vacuum, followed by transferring the resulting material into a reactor, adding isobutyraldehyde (200.0 g), stirring the mixture, reacting it at 90° C. for 0.6 hour, filtering off the reaction solution and analyzing the resulting filtrate according to gas chromatography. The results are as follows:
Conversion of isobutyraldehyde: 97.6%
Selectivity of CS-12: 87.0%
Yield of CS-12: 84.9%

Example 8

The reaction raw solution obtained in Example 5 was filtered according to a conventional method, and the resulting filtrate (150 g) was purified according to conventional rectification. The results are shown below.
Yield of CS-12: 135.2 g
Rectification efficiency: 97.2%

Example 9

White solids (7.3 g) obtained in the same manner as in Example 5 were calcined at 900° C. for 2 hours in vacuum, followed by transferring the resulting material into a reactor, adding isobutyraldehyde (600.0 g), stirring the mixture and reacting it at 80° C. for one hour, filtering off the reaction solution and analyzing the filtrate according to gas chromatography. The results are shown below.
Conversion of isobutyraldehyde: 95.4%
Selectivity of CS-12: 95.3%
Yield of CS-12: 90.9%

Example 10

White solids (7.3 g) obtained in the same manner as in Example 5 were calcined at 950° C. for 3 hours in vacuum, followed by transferring the calcined material into a reactor, adding isobutyraldehyde (600.0 g), stirring the mixture, reacting the mixture at 80° C. for 2 hours, filtering off the reaction solution and analyzing the filtrate according to gas chromatography. The results are shown below.
Conversion of isobutyraldehyde: 89.3%
Selectivity of CS-12: 95.2%
Yield of CS-12: 85.0%

Example 11

White solids (7.3 g) obtained in the same manner as in Example 5 were calcined at 1000° C. for 2 hours in nitrogen gas, followed by transferring the calcined material into a reactor, adding isobutyraldehyde (600.0 g), stirring the mixture, reacting at 80° C. for 1.2 hour, filtering off the reaction solution, and analyzing the filtrate according to gas chromatography. The results are shown below.
Conversion of isobutyraldehyde: 95.2%
Selectivity of CA-12: 94.8%
Yield of CS-12: 90.3%

Example 12

White solids (36.5 g) obtained in the same manner as in Example 5 were calcined at 1000° C. for 2 hours in air, followed by transferring the calcined material into a reactor, adding isobutyraldehyde (600.0 g), stirring the mixture, reacting it at 80° C. for 3 hours, filtering off the reaction solution and analyzing the filtrate according to gas chromatography. The results are shown below.
Conversion of isobutyraldehyde: 96.1%
Selectivity of CS-12: 93.1%
Yield of CS-12: 89.5%

Example 13

White solids (7.3 g) obtained in the same manner as in Example 5 were calcined at 800° C. for 3 hours in vacuum, followed by transferring the calcined material into a reactor, adding normal butyraldehyde (200.0 g), stirring the mixture, reacting it at 80° C. for 2 hours, filtering off the reaction solution and analyzing the filtrate according to gas chromatography. The results are shown below.
Conversion of normal butyraldehyde: 70.4%
Selectivity of 2-ethylhexenal: 89.2%
Yield of 2-ethylhexenal: 62.8%

Example 14

White solids (7.3 g) obtained in the same manner as in Example 7 were calcined at 800° C., for 3 hours in vacuum, followed by transferring the calcined material into a reactor, adding normal butyraldehyde (200.0 g), stirring the mixture, reacting it at 80° C., for 2 hours, filtering off the reaction solution and analyzing the filtrate according to gas chromatography. The results are shown below.
Conversion of normal butyraldehyde: 76.9%
Selectivity of 2-ethylhexenal: 85.2%
Yield of 2-ethylhexenal: 65.5%

Example 15

White solids (3.6 g) obtained in the same manner as in Example 5 were calcined at 800° C., for 3 hours in vacuum, followed by transferring the calcined material into a reactor, adding acetone (200.0 g), stirring the mixture and reacting it at 50° C., for 2 hours, filtering off the reaction solution and analyzing the filtrate according to gas chromatography. The results are shown below.

Conversion of acetone: 9.3%
Selectivity of diacetone alcohol: 90.9%
Yield of diacetone alcohol: 8.5%

Example 16

White solids (3.6 g) obtained in the same manner as in Example 7 were calcined at 800° C., for 3 hours in vacuum, followed by transferring the calcined material into a reactor, adding acetone (200.0 g), stirring the mixture, reacting it at 50° C. for 2 hours, filtering off the reaction solution and analyzing the filtrate according to gas chromatography. The results are shown below.
Conversion of acetone: 12.6%
Selectivity of diacetone alcohol: 87.1%
Yield of diacetone alcohol: 11.0%

Example 17

The reaction raw solution obtained in Example 14 was filtered according to a conventional method, followed by rectifying the resulting filtrate (150 g) according to conventional method. The results are shown below.
Yield of diacetone alcohol: 15.8%
Rectification efficiency: 95.8%

Comparative example 1

Magnesium oxide (MgO, made by Wako Junyaku) (4.0 g) was calcined at 700° C., for one hour in vacuum, followed by cooling the calcined material down to room temperature, transferring the total quantity of the compound into a reactor, adding isobutyraldehyde (200.0 g), stirring the mixture, reacting it at 110° C. for 15 hours, filtering off the reaction solution and analyzing the filtrate according to gas chromatography. The results are shown below.
Conversion of isobutyraldehyde: 0.1%
Selectivity of CS-12: 90.5%
Yield of CS-12: 0.009%

Comparative example 2

Barium oxide (BaO, made by Wako Junyaku) (4.0 g) and isobutyraldehyde were placed in a reactor, followed by stirring them, reacting it at 110° C. for one hour, filtering off the reaction solution and analyzing the filtrate according to gas chromatography. The results are shown below.
Conversion of isobutyraldehyde: 98.6%
Selectivity of CS-12: 20.8%
Yield of CS-12: 20.5%

Comparative example 3

Calcium carbonate ($CaCO_3$, made by Wako Junyaku) (3.7 g) was calcined at 900° C. for one hour in vacuum, followed by transferring the calcined material into a reactor, adding isobutyraldehyde (200.0 g), stirring the mixture, reacting it at 60° C. for 2.6 hours, filtering off the reaction solution and analyzing the filtrate according to gas chromatography. The results are shown below.
Conversion of isobutyraldehyde: 94.5%
Selectivity of CS-12: 56.2%
Yield of CS-12: 53.1%

Comparative example 4

Calcium nitrate tetrahydrate salt ($Ca(NO_3)_2 \cdot 4H_2O$ made by Wako Junyaku) (63.2 g) and barium nitrate ($Ba(NO_3)_2$, made by Wako Junyaku) (25.6 g) were dissolved in purified water (500 ml), followed by adding to the solution, a solution obtained by dissolving ammonium carbonate (($NH_4)_2CO_3$, made by Wako Junyaku) (42.1 g) in purified water (300 ml), filtering the resulting precipitate, water-washing and drying, to obtain a precursor of catalyst. The resulting white solids (6.2 g) were calcined at 900° C. for one hour in vacuum, followed by transferring the calcined material into a reactor, adding isobutyraldehyde (200.0 g), stirring the mixture, reacting it at 60° C. for 0.5 hour, filtering off the reaction solution and analyzing the filtrate according to gas chromatography. The results are shown below.
Conversion of isobutyraldehyde: 0.1%
Selectivity of CS-12: 70.3%
Yield of CS-12: 0.1%

Comparative example 5

Barium nitrate ($Ba(NO_3)_2$, made by Wako Junyaku) (52.2 g) was dissolved in purified water (300 ml), followed by adding to the resulting solution calcium oxide (CaO made by Wako Junyaku) (44.8 g), mixing them, drying the mixture at 140° C., calcining the resulting white solids (5.9 g) at 850° C. for 6 hours in air, transferring the total quantity thereof into a reactor, adding isobutyraldehyde (200.0 g), stirring the mixture, reacting it at 80° C. for 6 hours, filtering off the reaction solution and analyzing the filtrate according to gas chromatography. The results are shown below.
Conversion of isobutyraldehyde: 0.6%
Selectivity of CS-12: 83.2%
Yield of CS-12: 0.5%

Comparative example 6

Barium nitrate ($Ba(NO_3)_2$, made by Wako Junyaku) (52.2 g) was dissolved in purified water (300 ml), followed by adding to the resulting Solution calcium oxide (CaO made by Wako Junyaku) (44.8 g), mixing them, drying the mixture at 140° C., calcining the resulting white solids (5.9 g) at 850° C. for 6 hours in air, transferring the total quantity of the calcined material into a reactor, adding acetone (200.0 g), stirring the resulting mixture, reacting it at 80° C. for 6 hours, filtering off the reaction solution and analyzing the filtrate according to gas chromatography. The results are shown below.
Conversion of acetone: 1.1%
Selectivity of diacetone alcohol: 55.2%
Yield of diacetone alcohol: 0.6%

Comparative example 7

Barium nitrate ($Ba(NO_3)_2$, made by Wako Junyaku) (52.2 g) was dissolved in purified water (300 ml), followed by adding the resulting solution to calcium oxide (CaO, made by Wako Junyaku) (44.8 g), mixing them, drying the mixture at 140° C., calcining the resulting white solids (5.9 g) at 850° C. for 6 hours in air, transferring the total quantity of the calcined material into a reactor, adding normal butyraldehyde (200.0 g), stirring the mixture, reacting it at 80° C. for 6 hours, filtering off the reaction solution and analyzing the filtrate according to gas chromatography. The results are shown below.
Conversion of normal butyraldehyde: 1.1%
Selectivity of 2-ethylhexenal: 80.3%
Yield of 2-ethylehexenal: 0.8%
Effectiveness of the Invention When the use of the catalyst of the present invention is compared with the use of conventional catalyst, neutralization of the reaction solution and water washing are unnecessary; hence occurrence of waste water is zero and the objective product can be produced with a high efficiency and with a high yield. Thus, it is possible to achieve properties which could not have been effected by conventional catalysts, on a high level and at the same time. According to the present invention, it has been possible to provide such a catalyst, a process for producing the same and a process for producing a carbonyl compound derivative using the same. This fact is commercially, very meaningful.

What we claim:

1. A solid basic catalyst comprising barium and calcium as constituent elements thereof, the barium content thereof being 0.09 to 10% by weight, and the ratio of the calcium content to the barium content being in the range of 6.4 to 793 by weight.

2. A solid basic catalyst according to claim 1, wherein the solid basic catalyst is barium-supporting calcium oxide.

3. A solid basic catalyst according to claim 1, wherein said solid basic catalyst is a composite oxide of barium oxide and calcium oxide.

4. A solid basic catalyst composed of barium-supporting calcium oxide, obtained by adding at least one kind of nitrate, hydroxide or an organic acid salt of barium or an aqueous solution of the foregoing, to a suspension obtained by dispersing calcium hydroxide or calcium oxide or these compounds in water, followed by drying the resulting mixture and subjecting the dried material to thermal decomposition at 500° to 1200° C. in vacuum, an inert gas or air, barium being contained in a range of 0.1 to 10% by weight, and the ratio of the calcium content to the barium content being in the range of 6.4 to 793 by weight.

5. A solid basic catalyst composed of a composite oxide of barium oxide and calcium oxide, obtained by adding a compound containing carbonate ion, to an aqueous solution containing at least one kind of nitrate, hydroxide or an organic salt of barium and at least one kind of nitrate or an organic acid salt of calcium, followed by drying the resulting precipitate, and subjecting the dried material to thermal decomposition at 600° to 1200° C. in vacuum, an inert gas or air, barium being contained in a range of 0.09 to 9% by weight and calcium being contained in a ratio of the calcium content to the barium content of 7.2 to 793 by weight.

6. A solid basic catalyst composed of a composite oxide of barium oxide and calcium oxide, obtained by adding a compound containing carbonate ion, to a an aqueous solution containing at least one kind of nitrate, hydroxide or an organic acid salt of barium and at least one kind of nitrate or an organic acid salt of calcium, followed by drying the resulting precipitate, and subjecting the resulting precursor containing a calcium carbonate of vaterite structure, to thermal decomposition at 600° to 1200° C. in vacuum, an inert gas or air, barium being contained in a range of 0.09 to 9% by weight and calcium being contained in a ratio of the calcium content to the barium content of 7.2 to 793 by weight.

7. A solid basic catalyst composed of a composite oxide of barium oxide and calcium oxide, obtained by impregnating calcium carbonate with a an aqueous solution of at least one kind of nitrate, hydroxide or an organic acid salt of barium, followed by drying the resulting material, and subjecting the dried material to thermal decomposition at a temperature of 600° to 1200° C. in vacuum, an inert gas or air, barium being contained in 0.09 to 9% by weight and calcium being contained in a ratio of calcium content to barium content within a range of 7.2 to 793 by weight.

8. A process for producing a solid basic catalyst composed of barium-supporting calcium oxide, which process comprises adding an aqueous solution of at least one kind of nitrate, hydroxide or an organic acid salt of barium, to a suspension having calcium hydroxide or calcium oxide or these compounds dispersed in water, followed by drying the mixture and subjecting the dried material to thermal decomposition at 500° to 1200° C. in vacuum, an inert gas or air, barium being contained in a quantity of 0.09 to 9% by weight and the ratio of the calcium content to the barium content being in a range of 6.4 to 713 by weight.

9. A process for producing a solid basic catalyst composed of a composite oxide of barium oxide and calcium oxide, which process comprises adding a carbonate ion-containing compound to an aqueous solution composed of at least one kind of nitrate hydroxide or an organic acid salt of barium and nitrate, or an organic acid salt of calcium, followed by drying the resulting precipitate and subjecting the dried material to thermal decomposition at 600° to 1200° C. in vacuum, an inert gas or air, the barium content being 0.09 to 9% by weight and the ratio of the calcium content to the barium content being in the range of 7.2 to 793 by weight.

10. A process for producing a solid basic catalyst composed of a composite oxide of barium oxide and calcium oxide, which process comprises adding a carbonate ion-containing compound to a solution composed of at least one kind of nitrate, hydroxide or an organic acid salt of barium and at least one kind of nitrate or an organic acid salt of calcium, followed by drying the resulting precipitate and subjecting the resulting precursor containing calcium carbonate of vaterite structure to thermal decomposition at 600° to 1200° C. in vacuum, an inert gas or air, the barium content being 0.09 to 9% by weight and the ratio of the calcium content to the barium content being in the range of 7.2 to 793 by weight.

11. A process for producing a solid basic catalyst composed of a composite oxide of barium oxide and calcium oxide, which process comprises impregnating calcium carbonate with an aqueous solution composed of at least one kind of nitrate, hydroxide or an organic acid salt of barium, followed by drying the resulting material, and subjecting the resulting dried material to thermal decomposition at 600° to 1200° C. in vacuum, an inert gas or air, the barium content being 0.09 to 9% by weight, and the ratio of the calcium content to the barium content being in a range of 7.2 to 793 by weight.

* * * * *